United States Patent
Robichaud et al.

(10) Patent No.: US 11,701,150 B2
(45) Date of Patent: Jul. 18, 2023

(54) PATIENT-SPECIFIC FIXATION PLATE WITH SPACING ELEMENTS

(71) Applicant: LABORATOIRES BODYCAD INC., Québec (CA)

(72) Inventors: Jean Robichaud, St-Aubert (CA); Hugo Robichaud, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 281 days.

(21) Appl. No.: 16/609,953

(22) PCT Filed: Aug. 22, 2019

(86) PCT No.: PCT/CA2019/051153
§ 371 (c)(1),
(2) Date: Oct. 31, 2019

(87) PCT Pub. No.: WO2020/037423
PCT Pub. Date: Feb. 27, 2020

(65) Prior Publication Data
US 2021/0330363 A1    Oct. 28, 2021

Related U.S. Application Data

(60) Provisional application No. 62/722,403, filed on Aug. 24, 2018, provisional application No. 62/722,434, filed on Aug. 24, 2018.

(51) Int. Cl.
*A61B 17/80* (2006.01)
(52) U.S. Cl.
CPC .................. *A61B 17/8028* (2013.01)
(58) Field of Classification Search
CPC . A61B 17/8028; A61B 17/80; A61B 17/8004; A61B 17/8095
See application file for complete search history.

(56) References Cited

U.S. PATENT DOCUMENTS 2,002,021 A      5/1935  Rouse
4,338,926 A *    7/1982  Kummer ............ A61B 17/8028
                                                     606/62

(Continued)

FOREIGN PATENT DOCUMENTS

CN      103393459 A    11/2013
CN      207721848 U    8/2018
WO      WO-2015/003284 A2    1/2015

OTHER PUBLICATIONS

Azernikov S. (2013) Inhomogeneous Axial Deformation for Orthopedic Surgery Planning. in: Csurka G., Kraus M., Mestetskiy L., Richard P., Braz J. (eds) Computer Vision, Imaging and Computer Graphics. Theory and Applications. VISIGRAPP 2011. Communications in Computer and Information Science, vol. 274, p. 69-85. Springer, Berlin, Heidelberg.

(Continued)

*Primary Examiner* — Kevin T Truong
*Assistant Examiner* — Diana Jones
(74) *Attorney, Agent, or Firm* — Marshall, Gerstein & Borun LLP

(57) ABSTRACT

According to an aspect, a spacing element for spacing a fixation plate away from a bone to which the fixation plate is secured is provided. The spacing element has a body with a bone interface side and a plate interface side and sidewalls extending therebetween, said bone interface side having a bone contacting surface having contours conforming to surface contours of the bone. A corresponding fixation plate, fixation plate kit, and method for designing a patient-specific spacing element are also provided.

12 Claims, 4 Drawing Sheets

(56) References Cited

U.S. PATENT DOCUMENTS

| | | | |
|---|---|---|---|
| 4,957,497 A * | 9/1990 | Hoogland | A61B 17/80 606/71 |
| 5,013,315 A * | 5/1991 | Barrows | C08L 77/00 606/77 |
| 5,269,784 A * | 12/1993 | Mast | A61B 17/60 606/288 |
| 5,578,034 A * | 11/1996 | Estes | A61B 17/8047 411/909 |
| 5,620,448 A | 4/1997 | Puddu | |
| 5,749,875 A | 5/1998 | Puddu | |
| 6,017,342 A | 1/2000 | Rinner | |
| 6,066,142 A | 5/2000 | Serbousek et al. | |
| 6,461,359 B1 | 10/2002 | Tribus et al. | |
| 6,540,746 B1 * | 4/2003 | Buhler | A61B 17/8047 606/907 |
| 6,692,498 B1 * | 2/2004 | Niiranen | A61L 31/10 606/70 |
| 7,794,467 B2 | 9/2010 | McGinley et al. | |
| 7,935,119 B2 | 5/2011 | Ammann et al. | |
| 8,083,746 B2 | 12/2011 | Novak | |
| 8,092,465 B2 | 1/2012 | Mtezger et al. | |
| 8,137,406 B2 | 3/2012 | Novak et al. | |
| 8,211,112 B2 | 7/2012 | Novak et al. | |
| 8,241,292 B2 | 8/2012 | Collazo | |
| 8,241,293 B2 | 8/2012 | Stone et al. | |
| 8,337,507 B2 | 12/2012 | Lang et al. | |
| 8,388,690 B2 | 3/2013 | Singhatat et al. | |
| 8,409,209 B2 | 4/2013 | Ammann et al. | |
| 8,484,001 B2 | 7/2013 | Glozman et al. | |
| 8,594,395 B2 | 11/2013 | Roose et al. | |
| 8,632,547 B2 | 1/2014 | Maxson et al. | |
| 8,709,052 B2 | 4/2014 | Ammann et al. | |
| 8,753,348 B2 | 6/2014 | DiDomenico et al. | |
| 8,828,087 B2 | 9/2014 | Stone et al. | |
| 8,979,866 B2 | 3/2015 | Patel et al. | |
| 8,998,903 B2 | 4/2015 | Price et al. | |
| 9,014,835 B2 | 4/2015 | Azernikov et al. | |
| 9,072,555 B2 | 7/2015 | Michel | |
| 9,456,833 B2 | 10/2016 | Maxson et al. | |
| 9,480,490 B2 | 11/2016 | Meizger et al. | |
| 9,486,228 B2 | 11/2016 | Saw et al. | |
| 9,603,605 B2 | 3/2017 | Collazo | |
| 9,687,261 B2 | 6/2017 | Serbousek et al. | |
| 9,707,023 B2 | 7/2017 | Ammann et al. | |
| 9,770,302 B2 | 9/2017 | Kang et al. | |
| 9,814,533 B2 | 11/2017 | Park et al. | |
| 9,833,245 B2 | 12/2017 | Maxson | |
| 9,877,758 B2 | 1/2018 | Michel | |
| 9,877,790 B2 | 1/2018 | Bojarski et al. | |
| 9,943,348 B2 | 4/2018 | Schelling | |
| 10,245,089 B2 | 4/2019 | Paik | |
| 2005/0059873 A1 * | 3/2005 | Glozman | G06T 7/0012 600/407 |
| 2005/0209599 A1 | 9/2005 | Brunsvold | |
| 2006/0052795 A1 | 3/2006 | White | |
| 2007/0032882 A1 * | 2/2007 | Lodhi | A61L 27/34 623/23.76 |
| 2007/0055251 A1 * | 3/2007 | Huebner | A61B 17/8052 606/279 |
| 2007/0191848 A1 * | 8/2007 | Wack | A61B 17/80 606/279 |
| 2008/0317812 A1 * | 12/2008 | Zhang | A61B 17/8028 424/423 |
| 2009/0082816 A1 * | 3/2009 | Graham | A61B 17/8028 606/301 |
| 2011/0213376 A1 | 9/2011 | Maxson et al. | |
| 2012/0184960 A1 * | 7/2012 | Dosta | A61B 17/8028 606/281 |
| 2013/0338673 A1 | 12/2013 | Keppler | |
| 2015/0051650 A1 * | 2/2015 | Verstreken | G16Z 99/00 606/281 |
| 2015/0305752 A1 | 10/2015 | Eash | |
| 2016/0045234 A1 * | 2/2016 | Velikov | A61B 17/8028 606/285 |
| 2016/0095634 A1 | 4/2016 | Meyer | |
| 2016/0113784 A1 | 4/2016 | Robichaud | |
| 2016/0192949 A1 | 7/2016 | Robichaud et al. | |
| 2016/0235454 A1 | 8/2016 | Treace et al. | |
| 2016/0278827 A1 * | 9/2016 | Coelho Do Sameiro Espregueira Mendes | A61B 17/8061 |
| 2017/0325823 A1 | 11/2017 | Phillips-Hungerford et al. | |
| 2017/0325826 A1 | 11/2017 | Bake et al. | |

OTHER PUBLICATIONS

Azernikov et al., "Inhomogeneous Axial Deformation for Orthopedic Surgery Planning," Communications in Computer and Information Science, 274:69-85 (2013).

International Search Report and Written Opinion for Application No. PCT/CA2019/051147, dated Oct. 15, 2019.

International Search Report and Written Opinion for Application No. PCT/CA2019/051148, dated Oct. 24, 2019.

International Search Report and Written Opinion for Application No. PCT/CA2019/051149, dated Oct. 7, 2019.

International Search Report and Written Opinion for Application No. PCT/CA2019/051151, dated Oct. 22, 2019.

International Search Report and Written Opinion for Application No. PCT/CA2019/051153, dated Sep. 25, 2019.

International Search Report and Written Opinion for Application No. PCT/CA2019/051156, dated Sep. 30, 2019.

International Search Report and Written Opinion for Application No. PCT/CA2019/051157, dated Oct. 25, 2019.

\* cited by examiner

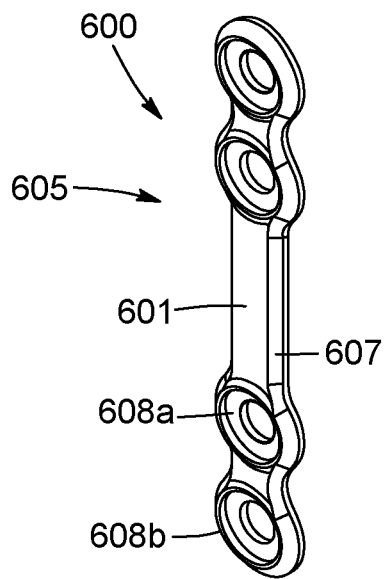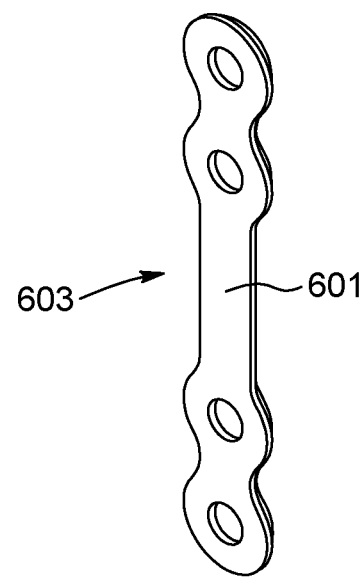
FIG. 4A  FIG. 4B
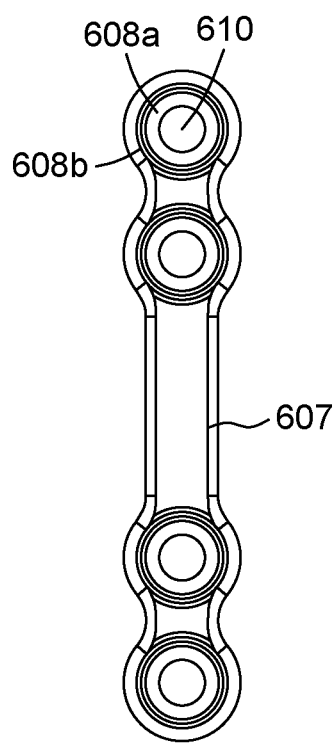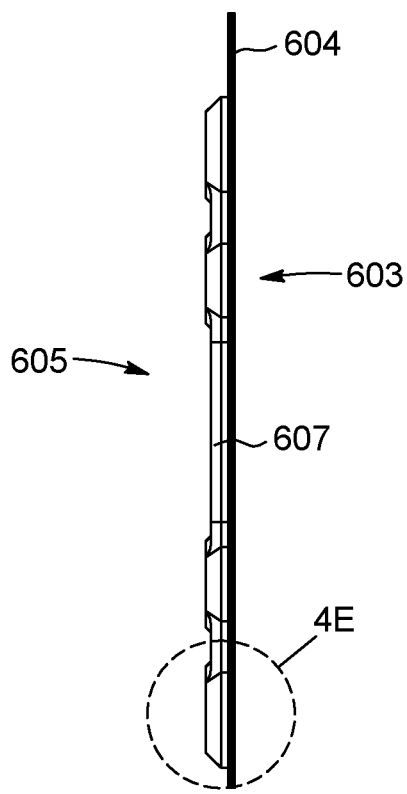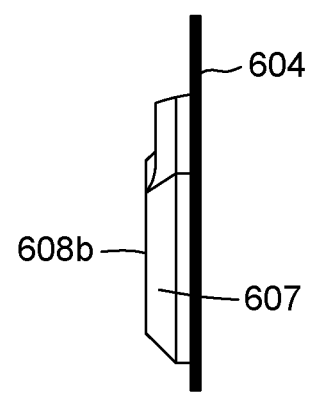
FIG. 4C  FIG. 4D  FIG. 4E

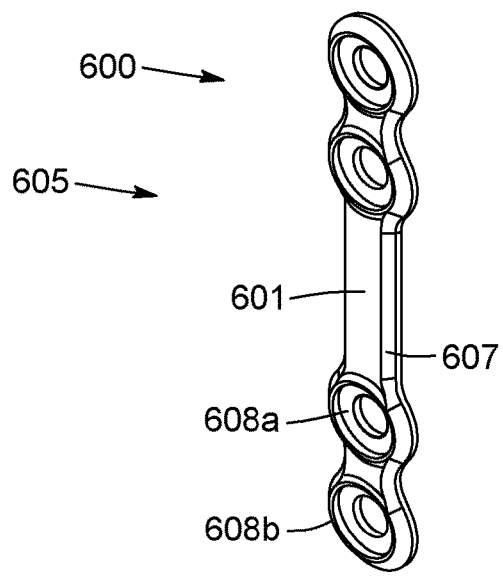
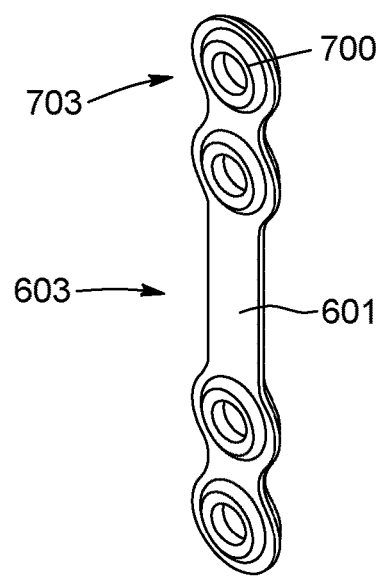
FIG. 5A  FIG. 5B
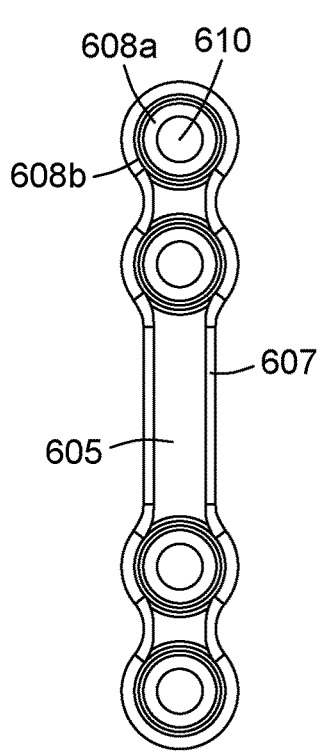
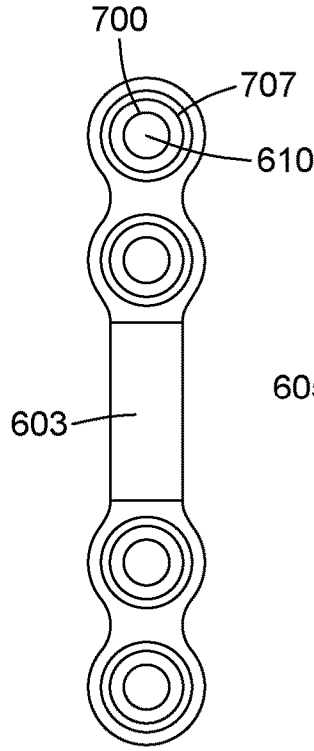
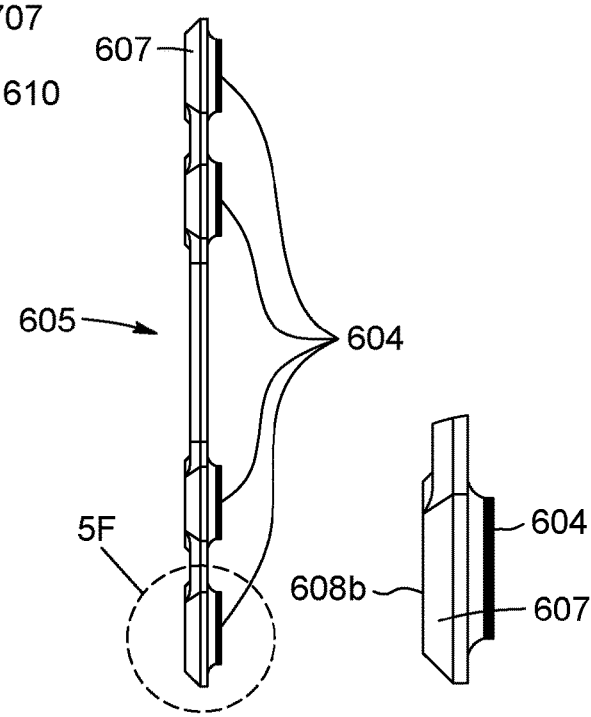
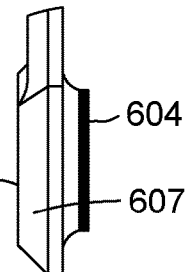
FIG. 5C  FIG. 5D  FIG. 5E  FIG. 5F

PATIENT-SPECIFIC FIXATION PLATE WITH SPACING ELEMENTS

RELATED APPLICATIONS

This application claims the benefit of U.S. Provisional Application No. 62/722,434, filed Aug. 24, 2018, entitled "PATIENT-SPECIFIC FIXATION PLATE WITH SPACING ELEMENTS FOR KNEE OSTEOTOMIES", and of U.S. Provisional Application No. 62/722,403, filed Aug. 24, 2018, entitled "SURGICAL KIT FOR KNEE OSTEOTOMIES AND CORRESPONDING PREOPERATIVE PLANNING METHOD", the entirety of which are incorporated herein by reference.

TECHNICAL FIELD

The technical field generally relates to tools used in knee osteotomy procedures, and more particularly in high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, a spacing element for spacing a fixation plate away from a bone to which the fixation plate is secured is provided. The spacing element has a body with a bone interface side and a plate interface side and sidewalls extending therebetween, said bone interface side having a bone contacting surface having contours conforming to surface contours of the bone.

According to an aspect, a fixation plate kit is provided. The fixation plate kit includes: a fixation plate having a body with a bone interface side and an outward facing side, the body having a plurality of fastener apertures defined therein for receiving fasteners to secure the fixation plate to a bone; and a plurality of spacing elements for positioning between the fixation plate and the bone when the fixation plate is secured to the bone, each of the spacing elements having a body with a bone interface side for contacting the bone, a plate interface side for contacting the plate, and sidewalls extending between the bone interface side and the plate interface side, the bone interface side of the spacing elements having a bone contacting surface with contours conforming to surface contours of the bone.

According to an aspect, a fixation plate for securing to a bone is provided. The fixation plate includes: a body having a bone interface side and an outward facing side, the bone interface side having surface contours conforming to surface contours of a predetermined position of the bone; and a plurality of spacing elements extending from the bone interface side for spacing the bone interface side of the body away from the bone when the fixation plate is secured thereto.

According to an aspect, a method for designing a patient-specific spacing element for a fixation plate is provided. The method includes: a) obtaining a 3D model of a patient's bone; b) determining an expected position of a fixation plate to be secured to the patient's bone; c) determining an expected position of a fastener in the fixation plate relative to the patient's bone; d) designing a spacing element having a body with a bone contacting surface, said bone contacting surface having contours conforming to surface contours of the bone at the expected position of the fastener; and e) manufacturing the spacing element according to the design.

BRIEF DESCRIPTION OF THE DRAWINGS

FIGS. 4A, 4B, 4C and 4D are respective front perspective, rear perspective, front and side views of a full contact plate, according to an embodiment; FIG. 4E is a detail view of a portion of FIG. 4D showing the contact surface and chamfered edge of the plate.

FIGS. 5A, 5B, 5C, 5D and 5E are respective front perspective, rear perspective, front, rear and side views of a low contact plate, according to an embodiment;

FIG. 5F is a detail view of a portion of FIG. 5E showing the contact surface and chamfered edge of the plate.

DETAILED DESCRIPTION

Figure 1A:
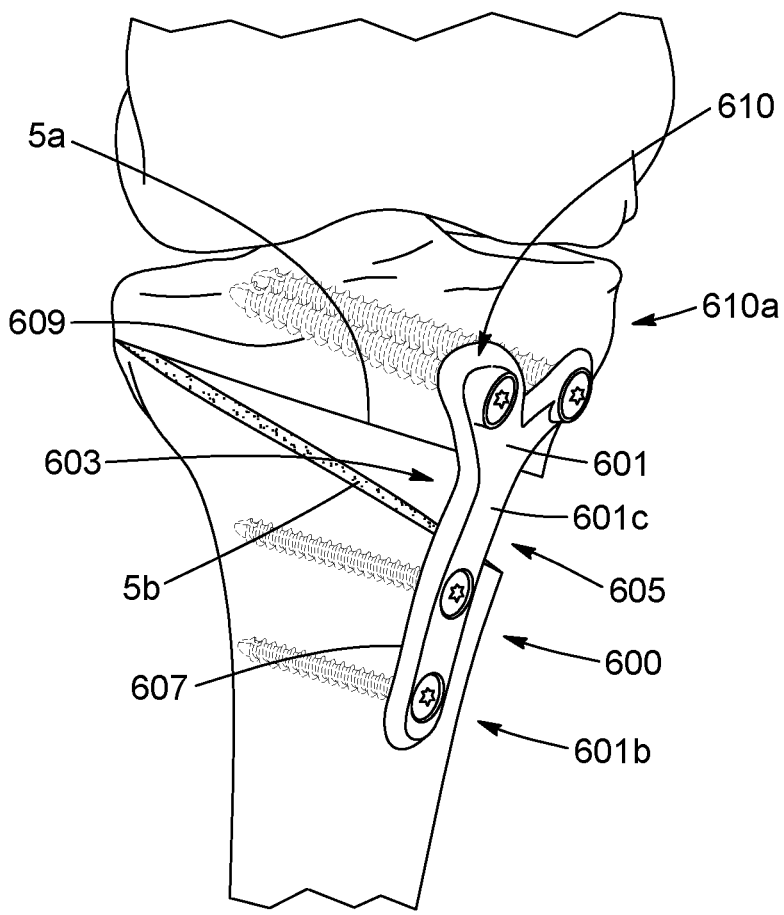
FIG. 1A is a perspective view of a fixation plate securing an open wedge formed in the patient's tibia bone, according to an embodiment.
Figure 1B:
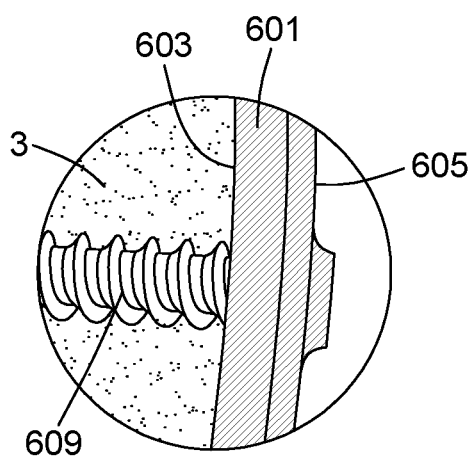
FIG. 1B is a partial-cross section detail view of the fixation plate secured directly to the patient's tibia bone via a fastener.

With reference to FIGS. 1A and 1B, a fixation plate 600 is shown. Fixation plate 600 comprises a body 601 made from a rigid, biocompatible and degradation-resistant material, such as stainless steel or titanium, although it is appreciated that other materials are possible, including different metals and/or plastics and/or a combination thereof. In the present embodiment, fixation plate 600 is an osteotomy plate for securing to an antero-medial side of a patient's tibia bone 3 and retaining the opening 7 formed therein during a high-tibial open-wedge osteotomy procedure. It is appreciated that in other embodiments, fixation plate 600 can be configured for securing to another side of the patient's bone 3 depending on surgical requirements. In the present embodiment, body 601 comprises a proximal section 601a for securing to the patient's bone 3 above opening 7, a distal section 601b for securing to the patient's bone 3 below opening 7, and an intermediate section 601c for spanning the opening 7. As will be described in more detail hereinafter, the present fixation plate 600 is patient-specific in that it has been designed based on the specific anatomy of the patient's bone 3 and based on the specific needs of the patient determined during a preoperative plan. The shape and configuration of fixation plate 600 can therefore vary from one procedure to another based upon the bone anatomy of different patients and based on their different needs.

The body 601 of fixation plate 600 is sized, shaped, and configured to fit snugly on the patient's bone 3 while also providing the required support and being minimally noticeable under the patient's skin. In the present embodiment, body 601 is thin and substantially flat, and is configured to follow the contours of the patient's bone 3. In this configuration, for example, when the fixation plate 600 is secured to the patient's bone 3, it can protrude from the surface of the patient's bone 3 at a uniform height along the entire body 601. Moreover, in some embodiments, body 601 can be designed to have a thickness which varies in different locations, allowing body 601 to have increased or reduced strength or rigidity where required and/or allow body 601 to protrude less noticeably from the patient's bone at certain areas.

The body 601 of fixation plate 600 comprises a bone interface side 603 and an outward-facing side 605. Bone interface side 603 comprises an inner surface for positioning adjacent the patient's bone 3. The contours of inner surface of bone interface side 603 are complementary in shape to surface contours of a predetermined position on the patient's bone 3. In this fashion, fixation plate 600 can fit snugly on a position of the patient's bone 3 determined preoperatively. Outward-facing side 605 is substantially smooth and/or flat to make it minimally noticeable under the patient's skin. In the present embodiment, the outward-facing side 605 comprises sloped and/or chamfered edges 607 which provide a smoother transition between the body 601 of fixation plate 600 and the patient's bone 3.

The fixation plate 600 is secured to the patient's bone 3 via fasteners 609. In the present embodiment, fasteners 609 comprise surgical screws which are drilled into the patient's bone 3, although it is appreciated that other type of fasteners are possible. The fasteners 609 engage with plate 600 via apertures or canals 610 opening on the bone interface side 603 and the outward facing side 605 of the plate 600. As can be appreciated, canals 610 can be sized and shaped to receive different sizes of fasteners 609. Moreover, canals 610 can be configured to guide fastener 609 at a predetermined angle or orientation as it is inserted into the patient's bone 3. For example, in the present embodiment, canals 610 comprise sidewalls extending through the thickness of the body 601 of plate 600 at a predetermined angle to guide the fasteners 609 as they are drilled through the canals 610. In some embodiments, the sidewalls of canals 610 can be threaded, for example to engage with corresponding threads of fasteners 609 as the fasteners 609 are being drill through canals 610, and/or to engage or lock with a head of the fasteners 609 once fully inserted. The sidewalls of canals 610 can further be configured to abut against a head of fastener 609 to block the fastener 609 from being inserted too deep into the patient's bone 3.

As can be appreciated, based on a preoperative plan, fixation plate 600 can be designed with a different number and configuration of canals 610 for receiving a different number and configuration of fasteners 609 based on the specific needs of the patient to promote optimal securing of the plate 600. Moreover, the fixation plate 600 can be configured such that it can accommodate combinations of different sizes of fasteners 609 (both diameter and length) and different orientation of fasteners 609, for example based on the position of the patient's bone 3 to which a particular fastener 609 is to be secured. In the illustrated embodiment, the plate 600 is configured to accommodate two large laterally-spaced fasteners 609 in the proximal section of body 601a, and two smaller vertically-spaced fasteners 609 in the distal section of body 601b. As can be appreciated, many other configurations of plate 600 are possible.

In the embodiment illustrated in FIG. 1B, the fixation plate 600 is in direct contact with the patient's bone 3. In other words, the inner surface of bone interface side 603 of fixation plate 600 abuts directly against the surface of the patient's bone 3. It is appreciated, however, that in other embodiments, the fixation plate (or section thereof) can be spaced apart from the patient's bone 3 and not be in direct contact therewith. Accordingly, bone interface side 603 can be configured to conform to surface contours of the patient's bone 3 at a predetermined spacing therefrom, and spacing elements can be provided to create a spacing between inner surface of bone interface side 603 and the surface of the patient's bone 3 when the fixation plate 600 is secured to the patient's bone 3.

Figure 2:
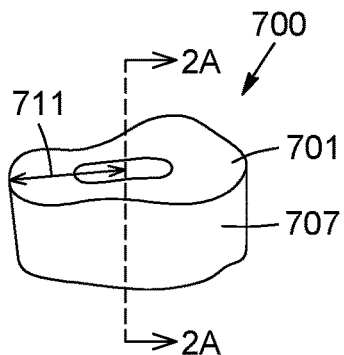
FIG. 2 is a perspective view of a spacing element, according to an embodiment.
Figure 2A:
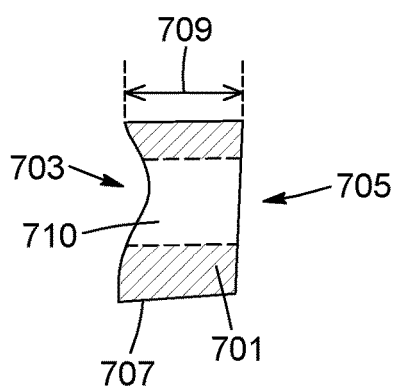
FIG. 2A is a cross sectional view of the spacing element of FIG. 2 taken along 2A-2A.

With reference to FIGS. 2 and 2A, a spacing element 700 for spacing a fixation plate from a patient's bone is shown according to an embodiment. Spacing element 700 comprises a body 701 made from a rigid, biocompatible material, such as metal, which can be the same or different material than fixation plate. Body 701 has a bone interface side 703 for contacting the patient's bone, and a plate interface side 705 for contacting the fixation plate. Sidewalls 707 extend between the bone interface side 703 and the plate interface side 705, defining a thickness 709 of the spacing element. The body 701 further defines a central aperture 710 for allowing a corresponding fastener to pass there-through. The central aperture extends through the thickness 709 of the body 701, and opens on the bone interface side 703 and the plate interface side 705. In the present embodiment, the body 701 is substantially cylindrical in shape, with a radius 711. It is appreciated, however, that other shapes are also possible. For example, in some embodiments, body 701 can be frustoconical in shape, and can have a radius 711 which varies along thickness 709.

In the present embodiment, the spacing element 700 is custom made to conform to the specific anatomy of a patient's bone. More specifically, the bone interface side 703 comprises a surface having contours conforming to the surface contours of the patient's bone. As can be appreciated, the position of spacing element 700 can be determined during pre-operative planning using a 3D model of the patient's bone, and the surface of bone interface side 703 can be configured to conform to the patient's bone at the determined position, such that the spacing element 700 fits snugly against the patient's bone at a specific position and orientation. The thickness 709 and radius 711 of spacing element 700 can further be adjusted based on patient-specific requirements. For example, as will be discussed in more detail below, thickness 709 can be adjusted to create a larger or smaller spacing distance, and radius 711 can be adjusted to increase or decrease the surface area of spacing element 700 in contact with the patient's bone and/or the fixation plate. In the present embodiment, the surface of plate interface side 705 is substantially flat and planar, however it is appreciated that in other embodiments, it can be configured to conform to a particular contour of the plate. Moreover, in some embodiments, plate interface side 705 and/or sidewalls 707 can be shaped and configured to key into fixation plate, for example to assure proper alignment and relative orientation of spacing element 700 and fixation plate. In some embodiments, interface side 705 can be configured to removably adhere or secure to fixation plate.

Figure 3:
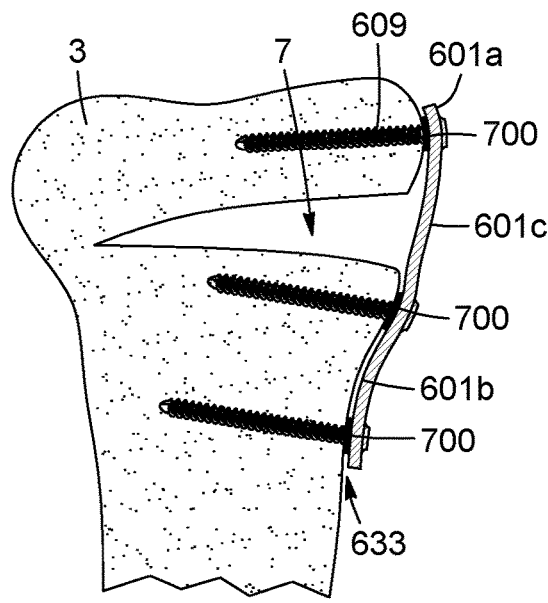
FIG. 3 is a cross sectional view of a fixation plate secured to a patient's tibia bone via fasteners using spacing elements, according to an embodiment.

With reference to FIG. 3, spacing element 700 is positioned between the fixation plate 600 and the patient's bone 3 to create a spacing 633 there-between. In the present embodiment, a plurality of spacing elements 700 is provided. Each of the spacing elements 700 is aligned with a corresponding fastener 609 and is specifically configured to conform to a particular position on the patient's bone 3. Each fastener 609 extends through the fixation plate 600 and through a corresponding spacing element 700 before securing in the bone 3. In the present embodiment, a spacing element 700 is provided for each fastener 609, although it is appreciated that in other embodiments, spacing elements 700 can be provided for only some of the fasteners 609. In the present embodiment, the spacing elements 700 are positioned relative to the fixation plate 600 during the surgical procedure, although it is appreciated that in other embodiments, spacing elements 700 can be pre-adhered to fixation plate 600.

Figure 3A:
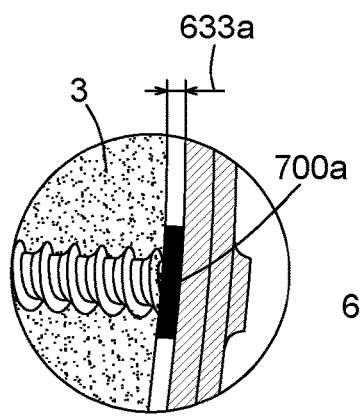
FIGS. 3A, 3B and 3C are partial-cross section detail views of the fixation plate spaced apart from the patient's bone at different distances via different sizes of spacing elements.
Figure 3B:
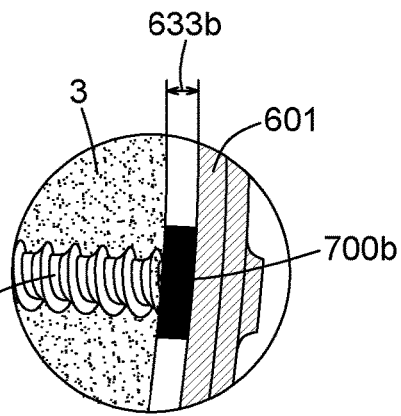
Figure 3C:
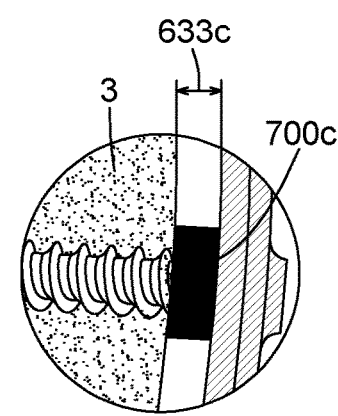

As can be appreciated, the number and configuration of the spacing elements 700 can be selected based on patient-specific spacing requirements. For example, in the present embodiment, spacing elements 700 are configured to provide a spacing 633 of approximately 2 mm. However, as illustrated in FIGS. 3A, 3B and 3C, other embodiments of spacing elements 700a, 700b, 700c can have different thicknesses 709 to provide different spacing distances 633a, 633b, 633c, for example within the range of approximately 1.8 mm to 2.2 mm. In the embodiment illustrated in FIG. 3, the spacing elements 700 are configured to provide a consistent or uniform spacing along the entire area of fixation plate 600. However, it is appreciated that in other embodiments, plate 600 and spacing elements 700 can be configured such that some sections of spacing plate 600 are spaced further apart from the patient's bone 3 than other sections. For example, proximal section 601a can be spaced away from bone 3 at a first spacing distance 633a, whereas distal section 601b can be spaced away from bone 3 at a second spacing distance 633b. Accordingly, a single plate 600 can be secured to bone 3 using a plurality of spacing elements 700 having different thicknesses. Moreover, in some embodiments, the spacing elements 700 used for the same plate 600 can have different radii 711, such that some spacing elements 700 have larger bone-contacting surfaces than others.

In the above-described embodiments, spacing elements 700 are independent from plate 600 in that they are not integrally formed as part of plate body 601. Instead, the described spacing elements 700 can be removable and/or repositionable relative to plate 600 and/or can be made from different materials than plate 600. It is appreciated, however, that in other embodiments, spacing elements 700 can be integrally formed as part of plate 600. Accordingly, a plate with integrally formed spacing elements 700 can be referred to a low contact plate, in that the plate is configured to have a bone interface side with reduced contact surface area with the patient's bone 3 by way of spacing elements 700. In contrast, a plate without spacing elements can be referred to as a full contact plate, in that the bone interface side will be in full contact with the patient's bone 3.

With reference to FIGS. 4A, 4B, 4C, 4D and 4E, an exemplary full contact plate 600 is shown according to an embodiment. In the illustrated embodiment, the plate 600 comprises a body 601 with a bone interface side 603 opposite an outward facing side 605. Fastener aperture 610 extend through body 601 and open on the bone interface 603 and outward facing 605 sides. As can be appreciated, the bone interface side 603 is substantially flat and featureless (i.e. without bumps, protrusions, etc.), defining a continuous or unbroken bone contacting surface 604 extending substantially throughout the entirety of the bone interface side 603. Although in the present embodiment the bone interface side 603 is substantially planar, it is appreciated that this is for illustrative purposes only, and that in other embodiments the bone interface side 603 can follow the contours of the surface of a patient's bone 3 while having a flat and featureless surface to allow full and direct contact with the surface of the patient's bone 3.

In the present embodiment, outward facing side 605 is provided with surface features to allow for a smooth transition between the surface of the patient's bone 3 and the plate 600. A sloped or chamfered edge 607 extends around the perimeter of body 601 on outward facing side 605, providing a gradual transition between the bone interface side 603 and a highest point on the outward facing side 605. The plate 600 is further configured with annular recesses 608a and/or annular bumps or protrusions 608b around fastener apertures 610 on outward facing side 605. The recesses 608a and/or bumps 608b can allow for a fastener to be seated in plate 600 when engaged in aperture 610 and prevent the fastener from protruding from a highest point of outward facing side 605. As can be appreciated, this configuration can allow for a smooth transition between fastener head and plate 600.

An exemplary low contact plate 600 is shown according to an embodiment in FIGS. 5A, 5B, 5C, 5D, 5E and 5F. As can be appreciated the structure of low contact plate 600 is substantially similar to the full contact plate described above, including similar surface features on outward facing side 605. However, as best seen in FIGS. 5B, 5D, 5E and 5F, bone interface side 603 is provided with surface features in the form of annular bumps or protrusions around apertures 610, defining spacing elements 700. In the present embodiment, spacing elements 700 are integrally formed as part of plate body 601 and are formed from the same material. It is appreciated, however, that in other embodiments, spacing elements 700 can be fused to body 601 and/or can be made of a different material. As can be appreciated, spacing elements 700 define a plurality of bone contacting surfaces 604 on bone interface side 603. This can reduce the overall area of plate body 601 in contact with the patient's bone 3, as the plate will only contact the bone along the surface 604 of spacing elements 700, rather than along the entirety of the bone interface side 603. It should be appreciated that in the present embodiment, bone contacting surfaces 604 on spacing elements 700 are substantially planar for illustrative purposes only. In other embodiments, the bone contacting surfaces 604 on spacing elements 700 can be shaped to conform to the surface contours of the patient's bone 3 to assure full contact between surface 604 and the surface of the patient's bone 3. Finally, although in the present embodiment spacing elements 700 are provided as annular surface features around apertures 610, it should be appreciated that in other embodiments, the surface features defining spacing elements 700 can be provided elsewhere on bone interface side 603 of plate 600.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A fixation plate kit comprising:
   a fixation plate made from a rigid and biocompatible material and comprising:
      a plate body having a bone interface side and an outward facing side;
      a plurality of fastener apertures defined therein for receiving fasteners to secure the fixation plate to a bone; and
      a plurality of spacing elements protruding outwardly from the bone interface side of the plate body in general alignment with a corresponding one of the plurality of fastener apertures such that each one of the fastener apertures extends through the plate body and a respective one of the plurality of spacing elements,
   the plurality of spacing elements being made of the same rigid and biocompatible material, and being integrally formed as a single piece with the plate body, the plurality of spacing elements being positioned between the plate body and the bone when the fixation plate is secured to the bone, each of the spacing elements having a spacing element body protruding outwardly from the bone interface side in spaced-apart relation with other spacing element bodies, each spacing element body having a bone interface side for contacting the bone and sidewalls extending between the bone interface side and the bone interface side of the plate body, the bone interface side of the spacing elements having a bone contacting surface with contours complementary in shape to surface contours of the bone, and each of the spacing elements having a thickness corresponding to a spacing distance between the bone interface side of the plate body at a position of a fastener to be received in the fixation plate and the patient's bone.

2. The fixation plate kit according to claim 1, wherein the fixation plate is configured to be secured in a predetermined position on the bone, further wherein the bone interface side of the spacing elements has contours following surface contours of the bone at the predetermined position.

3. The fixation plate kit according to claim 2, wherein the sidewalls of the spacing elements define thicknesses thereof, further wherein each of the plurality of spacing elements is configured with a thickness to provide a uniform spacing between the bone and the bone interface side of the plate body.

4. The fixation plate kit according to claim 1, wherein each of the plurality of spacing elements is configured to interface with the bone at predetermined positions relative thereto, further wherein the bone contacting surfaces of the plurality of spacing elements have surface contours complementary in shape to the surface contours of the bone at the predetermined positions.

5. The fixation plate kit according to claim 1, wherein the fixation plate is made from stainless steel or titanium.

6. The fixation plate kit according to claim 1, wherein the fixation plate is adapted to be secured to a patient's tibial bone as part of a knee osteotomy procedure.

7. A fixation plate for securing to a patient's bone at a predetermined position, the fixation plate comprising:
   a plate body having a bone interface side and an outward facing side; and
   a plurality of spacing elements having respective spacing element bodies protruding from the bone interface side in spaced-apart relation to one another for spacing the bone interface side of the plate body away from the patient's bone when the fixation plate is secured thereto, each one of the spacing elements being integrally formed as a single piece with the plate body, with the plate body and the spacing elements being made of a rigid and biocompatible material, each one of the spacing elements having a bone interface side with a bone contacting surface having surface contours complementary in shape to surface contours of the patient's bone in the predetermined position, wherein the plate body and the spacing elements are made of a same rigid and biocompatible material, and wherein each of the spacing elements has a thickness corresponding to a spacing distance between the bone interface side of the plate body at a position of a fastener to be received in the fixation plate and the patient's bone.

8. The fixation plate according to claim 7, wherein at least a portion of the bone contacting surface includes contours complementary in shape to the surface contours of the bone in the predetermined position.

9. The fixation plate according to claim 7, wherein the fixation plate has a plurality of fastener apertures defined therein for receiving fasteners to secure the fixation plate to the bone, further wherein each one of the fastener apertures extend through the plate body and a respective one of the spacing elements.

10. The fixation plate according to claim 7, wherein the plate body and the spacing elements are made from stainless steel or titanium.

11. The fixation plate according to claim 7, wherein the fixation plate is adapted to be secured to a patient's tibial bone as part of a knee osteotomy procedure.

12. A method for designing a patient-specific fixation plate, comprising:
   a) obtaining a 3D model of a patient's bone;
   b) determining an expected position of a fixation plate to be secured to the patient's bone;
   c) determining an expected position of a fastener to be received in the fixation plate relative to the patient's bone;
   d) determining a spacing distance of a plate body at the expected position of the fastener;
   e) designing the fixation plate including the plate body and a spacing element with a bone contacting surface, the fixation plate having a fastener aperture extending through the plate body and the spacing element at the expected position of the fastener and with the spacing element surrounding the fastener aperture, the spacing element having a thickness corresponding to the spacing distance, said bone contacting surface of the spacing element having contours complementary in shape to surface contours of the bone around the expected position of the fastener; and
   f) manufacturing the fixation plate as a single piece according to the design.

* * * * *